United States Patent [19]

Coss et al.

[11] Patent Number: 5,655,906
[45] Date of Patent: Aug. 12, 1997

[54] AUTOCLAVABLE DENTAL SONIC SCALER

[75] Inventors: Ronald G. Coss, Newport Beach; James L. Bocox, Rancho Santa Margarita, both of Calif.

[73] Assignee: Micro Motors, Inc., Santa Ana, Calif.

[21] Appl. No.: 489,494

[22] Filed: Jun. 12, 1995

[51] Int. Cl.[6] .................. A61C 1/05; A61C 1/07; A61C 1/08
[52] U.S. Cl. .................. 433/115; 433/119; 433/126
[58] Field of Search .................. 433/114, 115, 433/116, 117, 126, 119

[56] References Cited

U.S. PATENT DOCUMENTS

| 684,951 | 10/1901 | Rothkranz . |
| 866,518 | 9/1907 | Repsold .................. 433/116 |
| 1,485,963 | 3/1924 | Curry . |
| 1,517,186 | 11/1924 | Bond . |
| 2,709,852 | 6/1955 | Maurer et al. . |
| 3,488,851 | 1/1970 | Haydu . |
| 3,542,572 | 11/1970 | Edwardson .................. 433/116 |
| 3,654,502 | 4/1972 | Carmona et al. . |
| 4,110,908 | 9/1978 | Cranston . |
| 4,330,282 | 5/1982 | Nash . |
| 4,403,956 | 9/1983 | Nakanishi . |
| 4,589,847 | 5/1986 | Loge et al. .................. 433/126 |
| 4,619,612 | 10/1986 | Weber et al. . |
| 4,661,060 | 4/1987 | Strohmaier .................. 433/126 X |
| 4,757,381 | 7/1988 | Cooper et al. . |
| 5,062,832 | 11/1991 | Seghi . |
| 5,074,788 | 12/1991 | Nakanishi .................. 433/115 |
| 5,124,797 | 6/1992 | Williams et al. . |
| 5,382,162 | 1/1995 | Sharp . |

*Primary Examiner*—Nicholas D. Lucchesi
*Attorney, Agent, or Firm*—Knobbe, Martens, Olson & Bear, LLP

[57] ABSTRACT

The drive assembly for a dental sonic scaler is disconnected from a scaling tip assembly and is then withdrawn from a surrounding tubular handle/sheath. This allows the sheath to be sterilized, after use, while the drive assembly, not needing sterilization, can be easily connected to another sheath, by way of a quick-disconnect joining the components. A tubular seal between the tip assembly and the sheath prevent the drive assembly from being contaminated during use of the scaler.

13 Claims, 3 Drawing Sheets

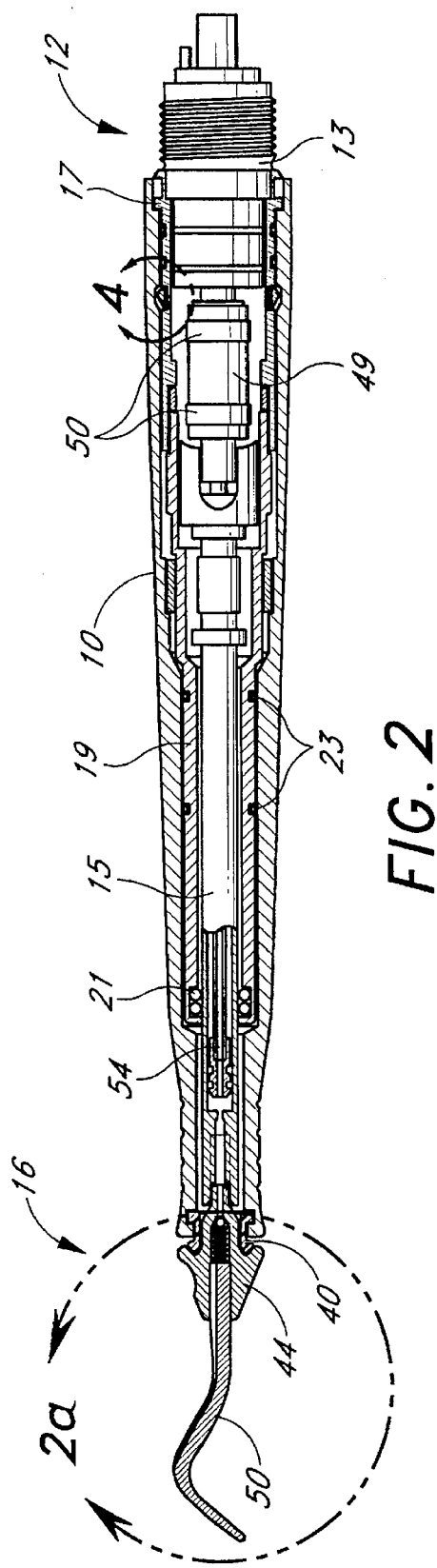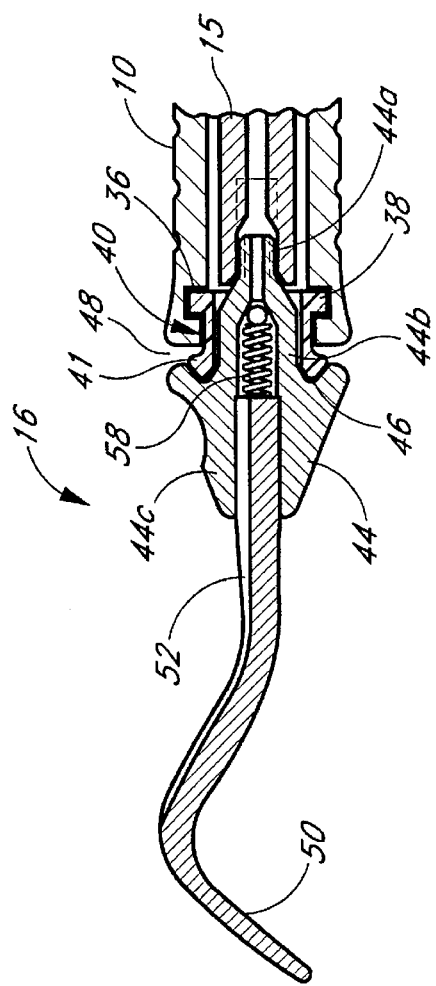

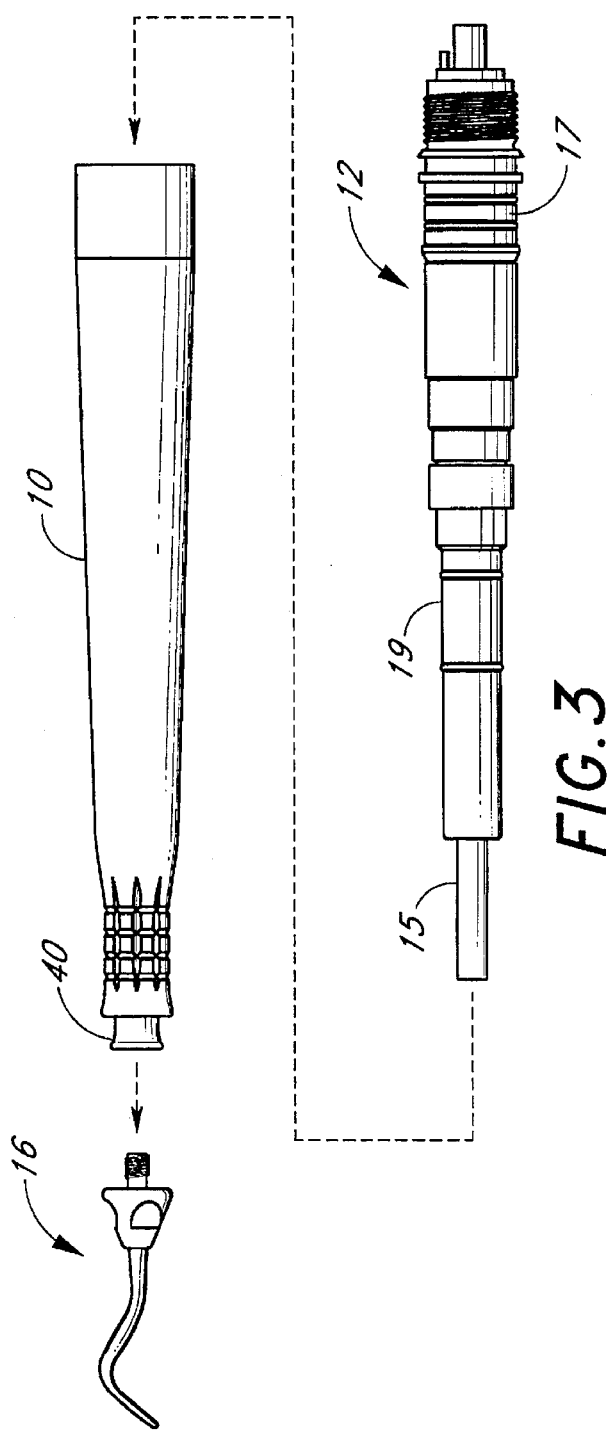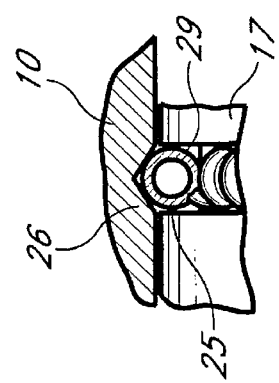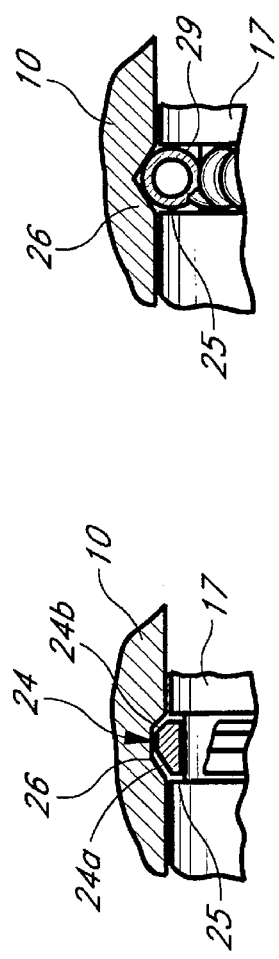

AUTOCLAVABLE DENTAL SONIC SCALER

BACKGROUND OF THE INVENTION

1. Field of the Invention

This invention relates to the fabrication and use of a dental sonic scaler used for cleaning teeth.

2. Prior Art

Sonic scalers are commonly used in dental facilities to clean plaque, tartar and other hard deposits from the teeth of patients. The sonic scalers usually consist of a hand held drive assembly with a rapidly vibrating tip driven by compressed air. The drive assembly converts the energy from the compressed air to a high frequency movement of the tip.

The tip which is made of a rigid material, rapidly vibrates to remove deposits from the tooth surfaces. The shape of the tip is often hook shaped to assist the user in reaching hard to reach locations between the teeth.

Scalers are now recommended to be sterilized after each use. The recent spread of infectious diseases, such as HIV, has raised the level of care given to sterilizing dental equipment between patients. Because bodily fluids reach the exterior surface of the drive assembly, that surface must be sterilized.

The common approach to sterilize the exterior surface of the drive assembly has been to insert the entire scaler into an autoclave for steam sterilization. Autoclaving the entire scaler at high temperature results in rapid deterioration of the internal rubber components such as the o-rings and a mounting grommet used to mount the drive assembly and isolate the vibration from the outer housing. This deterioration diminishes the performance by reducing the strength of the vibrations. Repeated replacement of these components is expensive and raises the cost of maintaining the dental equipment. Further, replacing these components is troublesome.

Another problem with autoclaving the entire scaler is that it forces the user to maintain several drive assemblies so that the user can continue to work while some of the scalers are being sterilized.

As one solution to the problem, some users have been disassembling scalers of the general type shown in U.S. Pat. No. 4,330,282, and only sterilizing the exterior housing and the tip components that are exposed to the patient. This prevents degradation of the internal components, but it is time consuming to disassemble and then reassemble after sterilization. Also, some users are not adept at such operations. Further, an annular gap between the housing and the vibrating tip allows contaminants to enter the forward end of the housing.

U.S. Pat. No. 5,382,162 is directed to an ultrasonic dental scaler which includes a handpiece having an outer sheath that can be unthreaded from an electronic drive unit. The sheath can then be separately sterilized. While that approach is an improvement over sterilizing the entire unit, the unthreading operations to expose the internal drive coil takes some time. Also, the vibrating unit, a rather long rod attached to the vibrating tip, must be sterilized. In addition, the prevention of fluid into the drive unit relies on an o-ring positioned between the rod and a surrounding housing.

It is a primary object of this invention to provide a sonic scaler design that is able to be reliably sterilized repeatedly without affecting performance. Also, it is a goal to prevent contaminants from entering the forward end of the tool while isolating the handle from the vibrating tip of the tool. Minimizing the number of extra drive assemblies a dentist must maintain is also a desirable feature of the invention. Finally, the scaler should be as easy to maintain and use as current sonic scalers, and also be reasonably priced.

SUMMARY OF THE INVENTION

Briefly stated, the dental scaler of the invention includes a sonic drive assembly encased within a sheath adapted to be conveniently gripped by an operator in cleaning a person's teeth. A forward end of the drive assembly is releasably connected to a rigid tooth cleaning tip. A flexible tubular boot or seal creates a seal between the tip and the sheath so as to prevent fluids from entering the sheath and engage the drive assembly but not affect the power of the vibrations. One end of the tubular seal surrounds a rear portion of the tip compressed against the rear of a flange on the tip and another end is secured to the forward end of the sheath. The tip is easily removable for sterilization. Once the tip is removed, the sheath is easily separable from the enclosed drive assembly by means of a push-pull, quick disconnect arrangement. This enables the sheath to be separately cleaned and sterilized while the drive assembly, not having been contaminated, can be reinserted into a sterilized sheath and connected to a sterilized tip for use with the next patient.

Advantageously, autoclaving only the sheath portion of the drive assembly prevents the seals and other components within the drive assembly from being adversely affected by sterilization procedures. Further, the dentist only needs to maintain multiple sheaths, which saves significantly on cost.

BRIEF DESCRIPTION OF THE DRAWINGS

FIG. 2 is a side elevational view of an external sheath of the scaler of FIG. 1, partially in cross section.

FIG. 2a is a side cross-sectional view illustrating the connection between the sheath, a tooth scaling tip, and a tubular seal.

FIG. 3 is a side elevational exploded view of the sheath and the drive assembly of the scaler of FIG. 1.

FIG. 4 is an enlarged cross-sectional view of a portion of a housing for the drive assembly, illustrating one way to join the assembly to the sheath in a quick disconnect fashion.

FIG. 5 is a cross-sectional, fragmentary view illustrating an alternate means of securing the drive assembly to the sheath in a quick disconnect fashion.

DETAILED DESCRIPTION OF THE PREFERRED EMBODIMENT

Figure 1:
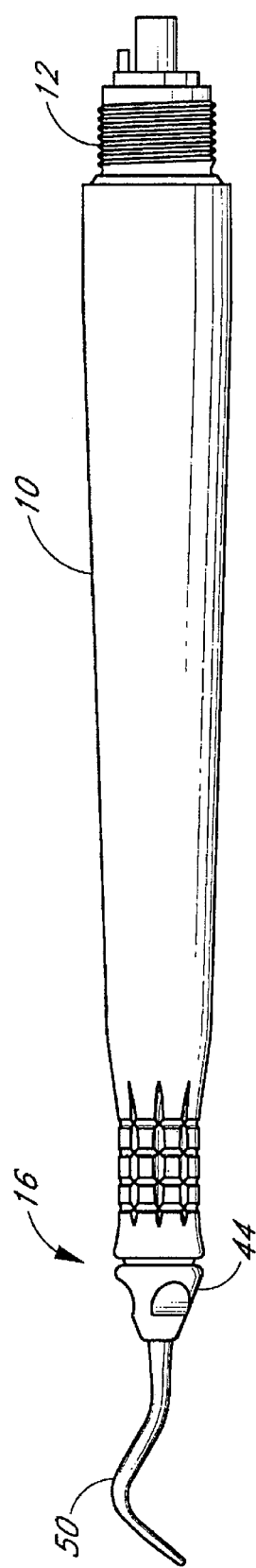
FIG. 1 is a side elevational view of an assembled scaler.

Referring to FIG. 1, there is illustrated a dental scaling tool utilized for cleaning teeth. The device includes an exterior sheath 10 housing a drive assembly 12, a portion of which is shown protruding from the rear of the sheath, and a cleaning tip assembly 16 attached to the drive assembly at the forward end of the sheath 10. The rear of the drive assembly 12 is adapted to be connected to a source of compressed air which drives the power unit to produce vibration of the tip 16 assembly at sonic frequency. An exhaust air outlet is also formed in the rear of the power unit. In addition, the unit is adapted to be connected to a source of water for cleaning and cooling the sonic tip. The apparatus for providing the compressed air and the water is not illustrated in the drawings inasmuch as standard, well-known components are available for this purpose.

In FIG. 2, the drive unit 12 includes a head assembly 13 connected on its forward end to an elongated tubular shaft 15. The head assembly 13 is positioned within a rear tubular body 17 which is threadably connected on its forward end to a shaft housing 19 which surrounds the rear portion of the tubular shaft 15. As seen from FIG. 2, the shaft 15 extends through the shaft housing 19 and terminates near the forward end of the sheath 10. A pair of O-rings 21 are shown confined within the forward end of the housing 19 and surrounding the drive shaft 15. A resilient mounting grommet 49 connects the rear of the shaft 15 to the head assembly 13 by means of 2 crimped ferrules 50. The head assembly 13 is connected by suitable fasteners, not shown, to the rear body 17. With this arrangement, the drive assembly 12 may be removed as a unit from the sheath 10, as seen in FIG. 3.

As can be seen from FIG. 2, the interior of the sheath has a series of cylindrical sections sized to fit the various diameters of the drive assembly. A pair of O-rings 23 or other suitable means is positioned within spaced annular grooves in the shaft housing 19 and extend between the shaft housing and the interior of the sheath to provide a seal in that area and support for the sheath.

In accordance with one aspect of the invention, the drive assembly 12 is captured within the sheath in a manner by which it can be easily connected and disconnected, by suitable means. In the arrangement of FIG. 2 and 4, there is provided an annular groove 25 in the exterior of the housing. An annular groove 26 is formed in the interior of the sheath, and is radially aligned with the groove 25 in the housing when the drive assembly 12 is fully installed within the sheath 10. A retainer or detent spring 24 is positioned within the annular channel formed by the housing groove and sheath groove. The retainer spring 24 is a partial ring, having a gap in its circumference to enable it to be spread and positioned in the channel. The spring has a cross section with a tapered forward edge and tapered rear edge 24b that enable the drive assembly to be inserted or removed from the sheath by simply providing relative pushing or pulling motion on the mating components.

As a preferred retainer, there is shown in FIG. 5 a small diameter coil or garter spring 29 arranged in the form of a ring which fits within the channel formed by the grooves 25 in the rear body 17 and groove 26 in the sheath. As seen in FIG. 5, the groove 26 has a triangular cross section presenting sloping, leading and trailing surfaces to enable the spring 29 to be easily moved into and out of the groove 26. In its unstressed condition, the spring will hold the drive unit within the sheath. However, pushing or pulling on the drive shaft relative to the sheath will cause the coils of the garter spring to collapse sufficiently to allow the drive assembly to be inserted or withdrawn.

In accordance with another aspect of the invention, a flexible, sealed connection is formed between the forward end of the sheath 10 and the rear of the scaling tool assembly 16. This function is provided by a resilient, tubular seal or boot 40. As seen in FIG. 2a, the rear of the seal 40 has a thickened bead or ring-shaped portion 38 which fits within an annular groove 36 formed in the interior wall of the forward end of the sheath. The bead 38 preferably has a rectangular cross-section. The exterior diameter of the ring or bead 38 is sized to fit snugly within the groove 36, but it is flexible so that it can easily be squeezed to be inserted into the forward end of the sheath to allow the ring 38 to snap into position in the groove 36.

The main body of the tubular seal 40 is quite thin so as to be very flexible. In a prototype unit, the seal has a wall thickness of about 0.020 inch. The forward end of the seal also has a radially outwardly extending thickened bead or ring 41 having a circular cross-section adapted to mate with the tip assembly 16. More specifically, as seen from FIG. 2a, the tip assembly includes a tubular body 44 having a rear connector portion 44a which is threaded on its exterior so as to be threaded into the forward end of the tubular drive shaft 15. Adjacent the threaded section is a larger diameter cylindrical portion 44b which fits within the tubular seal 40. The tip body 44 further includes an enlarged tubular, conically shaped portion 44c which on its largest exterior diameter is about the same as the forward end of the sheath, which is larger than the exterior diameter of the forward end 41 of the seal.

The rear face of the conical portion is formed with an annular recess 46 which receives the forward bead 41 of the seal 40. The components are dimensioned so that when the tip is threaded into the forward end of the drive shaft 15, the tubular boot 40 is axially compressed, thereby creating a snug seal between the forward bead 41 and the annular recess 46 in the body portion 44c. The threaded engagement between the tip body 44 and the drive shaft is limited so that a gap, 48 bridged by the boot 40 remains between the rear of the conical tip portion 44c and the forward end of the sheath. The seal thus prevents fluids from entering the drive mechanism from the joint between the tip assembly 16 and the sheath 10. The flexible nature of the boot allows freedom of movement so that the tip assembly can vibrate but yet the vibration from the tip assembly is not transferred to the sheath.

The tubular seal may be made of a variety of materials that are sufficiently flexible and resilient, provide the necessary sealing function and are autoclavable, or else disposable from a practical standpoint. A prototype version of the seal was made of silicone having a 50 Shore A hardness rating.

The tip assembly 16 also includes a scaling element 50 which is fixed in the forward end of the tubular body 44. A groove 52 in the exterior of the element 50 opens into the interior of the body 44. A small chamber 56 in the tip body 44 extends between the rear of the tip 50 and a conical surface in the interior of the tip. A check valve element 58 in the chamber 56 is urged into closed position by a light spring 60.

In use, pressurized air applied to the drive assembly produces vibration of the scaling element 50 at sonic frequencies to be moved in contact with teeth to remove plaque and other materials. Cooling water is transmitted through a tube 54 in the tubular drive assembly 12 and through the tip assembly body 44, where it exits the forward end of the body flowing in the groove 52 on the exterior of the scaling element 50. The water flows along the tip of the element and onto the patient's tooth. The outward flow of this cooling water prevents any contaminated fluid from flowing rearwardly. The check valve 58 permits flow in the outward direction but prevents reverse flow. Since the water is under pressure to flow out the tip, the check valve is provided merely as a preventive in the event some contaminated fluid could enter the tool interior when water pressure is abruptly interrupted. The exterior of the tool as well as the exterior of the tubular seal and the exterior of the sheath are exposed to this water and any fluids from the patient. The fluids however do not reach the drive mechanism within the sheath, in view of the flexible tubular seal.

Referring to FIG. 3, when the cleaning operation for a patient is completed, the tip assembly 16 is disconnected from the drive assembly 12 by unthreading from the assembly 12. The drive assembly can then be withdrawn from the sheath by simply pulling on it with respect to the sheath. The tip, the tubular seal, and the sheath can then be sterilized while the drive unit is reused with a sterile sheath tubular seal and tip assembly. The tubular seal can be completely separated from the sheath for the sterilization operation, or can be left attached to the sheath.

What is claimed is:

1. A dental tool for cleaning teeth comprising:

a drive assembly;

a tubular sheath enclosing said assembly and sized to be gripped by an operator when utilizing the tool to clean teeth;

a tool tip assembly releasably connected to a forward end of said drive assembly to be vibrated by the drive assembly, the tip assembly including an element for engaging the teeth; and a flexible tubular boot surrounding a rear porton of said tip assembly and forming a seal between the tip assembly assembly and the sheath that prevents fluid from entering the sheath while permitting the tip to be vibrated by said drive assembly independently of said sheath.

2. The tool of claim 1, including a quick disconnect coupling between the drive assembly and the sheath that enables the drive assembly to be quickly installed in the sheath or removed from the sheath without the use of installation or removal equipment.

3. The tool of claim 2, wherein a rear portion of said boot is in sealing engagement with a forward portion of said sheath, and a forward portion of said boot is in sealing engagement with said tip assembly, and said tip assembly and said sheath remain spaced from each other when the tip assembly is fully installed in the drive assembly.

4. The tool of claim 2, wherein the coupling between said sheath and said drive assembly is connected or disconnected by relative axial pushing or pulling movement of the sheath and the drive assembly.

5. The tool of claim 4, wherein the coupling between the sheath and the drive assembly comprises a lock ring positioned in a channel formed by annular grooves in the interior of the sheath wall and the exterior of a drive assembly component.

6. The tool of claim 5, wherein said coupling comprises a resilient lock ring which in its normal position holds the sheath and the drive assembly together, but which is capable of being flexed into a smaller diameter ring by axial separating force between the drive assembly and the sheath.

7. The tool of claim 2, wherein said coupling comprises a small diameter coil spring shaped in the form of a ring that is captured in a channel formed by grooves in the interior of the sheath and the exterior of a drive assembly component, said spring having a locking position in which it holds the drive assembly within the sheath and having an unlock position wherein the ring diameter of the coil spring ring is decreased upon a relatively pushing and pulling movement between the sheath and the drive assembly to enable the drive assembly to be withdrawn from the sheath.

8. The tool of claim 1, wherein said tip assembly has a rearwardly facing annular recess adapted to receive a forward end of said tubular boot in sealing engagement with the boot upon attachment of the tool assembly to the drive assembly.

9. The tool of claim 8, wherein said drive assembly includes a shaft having a threaded tubular forward end adjacent the forward end of said sheath, said tip assembly has a rearward externally threaded portion adapted to be threaded into the forward end of said shaft, said boot being dimensioned such that it is axially compressed as said tip assembly is threadedly attached to said shaft.

10. The tool of claim 1, wherein said drive assembly includes a shaft having a threaded tubular forward end adjacent the forward end of said sheath, said tip assembly has a rearward externally threaded portion adapted to be threaded into the forward end of said shaft, said boot being dimensioned such that it is axially compressed as said tip assembly is threadedly attached to said shaft.

11. The tool of claim 1, wherein said sheath, said boot, and said tip are made of materials which can withstand repeated sterilization processes in an autoclave.

12. A dental tool for cleaning teeth comprising:

a drive assembly;

a tool tip assembly having a rear portion in driving engagement with a forward end of said tip assembly;

a tubular sheath surrounding said drive assembly;

a seal extending between said tool tip assembly and a forward end of said sheath to prevent fluid from leaking into the sheath or permitting vibration of said tool with respect to said sheath;

said sheath being connected to said drive assembly in a manner that permits the drive assembly to be quickly withdrawn from the sheath by simple manual force without the use of additional equipment, once the tip assembly has been connected from the drive assembly;

the drive assembly including a tubular housing that fits snugly within said sheath, and an annular groove on the exterior of the housing, and said sheath including a mating groove on the interior of the sheath, the groove defining an annular channel; and a detent spring in said channel having a connecting position in which the spring extends into both grooves and a reduced diameter disconnect position wherein the spring is positioned in only one of the grooves so as to allow the sheath to be pulled away from the drive assembly.

13. A method of sterilizing a dental scaler comprising the steps of:

disconnecting a tool tip assembly from a forward end of a drive assembly and in the process braking a seal between the tip assembly and the forward end of the sheath surrounding a scaler drive assembly;

withdrawing the drive assembly as a unit from the sheath with a simple manual force and without the use of additional equipment; and sterilizing the sheath without the need for sterilizing the drive assembly;

wherein the breaking of said seal includes withdrawing said tip assembly from within a tubular boot having a rear end in sealing engagement with said sheath and having a forward end which was in sealing engagement with an annular recess in said tip assembly.

* * * * *